United States Patent [19]
Pratt

[11] Patent Number: 5,836,880
[45] Date of Patent: Nov. 17, 1998

[54] AUTOMATED SYSTEM FOR MEASURING INTERNAL TISSUE CHARACTERISTICS IN FEED ANIMALS

[75] Inventor: William C. Pratt, Canyon, Tex.

[73] Assignee: Micro Chemical, Inc., Amarillo, Tex.

[21] Appl. No.: 748,220

[22] Filed: Nov. 12, 1996

Related U.S. Application Data

[63] Continuation-in-part of Ser. No. 395,931, Feb. 27, 1995, Pat. No. 5,573,002.
[51] Int. Cl.$^6$ ........................................................ A61B 8/00
[52] U.S. Cl. ............................................................ 600/443
[58] Field of Search ......................... 128/660.02, 660.03, 128/660.06, 660.07, 662.03, 662.06; 73/644; 600/443, 444, 445, 446, 447, 459, 442, 438, 449

[56] References Cited

U.S. PATENT DOCUMENTS

| | | |
|---|---|---|
| 4,359,055 | 11/1982 | Carlson . |
| 4,359,056 | 11/1982 | Carlson . |
| 4,844,080 | 7/1989 | Frass et al. . |
| 5,079,951 | 1/1992 | Raymond et al. . |
| 5,218,963 | 6/1993 | Mazess . |
| 5,303,708 | 4/1994 | Stouffer . |
| 5,353,796 | 10/1994 | Schroeder et al. . |

*Primary Examiner*—George Manuel
*Attorney, Agent, or Firm*—Klarquist Sparkman Campbell Leigh & Whinston, LLP

[57] ABSTRACT

An automated tissue analysis system is described comprising a conveyor for delivering a feed animal to a tissue analysis zone, an ultrasound transducer designed to conduct tissue analysis on feed animals, and a remotely actuated positioner for placing the transducer on the feed animal. The ultrasound transducer is coupled to the positioner. One embodiment of the positioner comprises a saddle, a longitudinal slide frame, a dorsal/ventral slide frame and a pivot frame for accurately positioning the transducer on the animal for conducting tissue analysis. A transducer housing is provided that includes a built-in fluid passage and dispenser for dispensing conductive fluid onto the animal from a remote fluid reservoir. A fluid pump is fluidly coupled to both the reservoir and the dispenser in the transducer housing so that fluid can be pumped from the reservoir to the dispenser. The tissue analysis systems also generally include a computer or computers operably coupled to individual components of the analysis system. This allows an operator to either control the components by inputting commands to the computer, or place the computer in control of the components. The computer also can store and analyze data generated by the transducer, and any other instruments that might be used in the analysis of feed animals that can be coupled to the positioner for remote actuation. By actuating joy-stick controls an operator can control all the components of the tissue analysis system. The apparatus can be used in combination with an overall animal management system such as might be found in a feedlot. The animal management system can sort animals, promote feed efficiency and optimize shipping dates for animals, either individually or in groups.

21 Claims, 9 Drawing Sheets

AUTOMATED SYSTEM FOR MEASURING INTERNAL TISSUE CHARACTERISTICS IN FEED ANIMALS

CROSS REFERENCE TO RELATED APPLICATION

This is a continuation-in-part of U.S. patent application Ser. No. 08/395,931, entitled METHOD AND APPARATUS FOR MEASURING INTERNAL TISSUE CHARACTERISTICS IN FEED ANIMALS (parent application), which was filed on Feb. 27, 1995 now U.S. Pat. No. 5,573,002. The parent application is incorporated herein by reference.

FIELD OF THE INVENTION

This invention concerns an ultrasound transducer for measuring internal tissue characteristics, such as backfat, marbling and muscle in livestock. The ultrasound transducer can be used in combination with an automated conveying and positioning system to provide an automated system useful for evaluating the health and tissue characteristics of feed animals.

BACKGROUND OF THE INVENTION

Feedlots promote animal growth and improve the quality of the animal prior to slaughter. Although some feedlots are designed to handle relatively few cattle, most of the feedlots in North America are considerably larger and accommodate thousands of animals. There is considerable diversity in individual animal characteristics, such as weight, frame size, fat content, fat deposition rate, intramuscular fat (marbling) and muscling within this feedlot cattle population. The producer's goal in using a feedlot is to optimize the growth rate and food value characteristics of each animal prior to slaughter. Achieving this goal ideally requires obtaining physical data and growth characteristics for each animal at multiple times during its stay in the feedlot.

Some of these measurements have been made using probe-like instruments. For instance, backfat has been measured by piercing the skin of the animal and taking physical measurements. This clearly aggravates the animal and may be illegal in certain areas. See Carlson's U.S. Pat. Nos. 4,359,055 and 4,359,056. Ultrasound techniques have been developed to replace these physically invasive and time-consuming methods. Ultrasonic devices transmit ultrasonic waves into the animal. Ultrasonic waves are transmitted and reflected by muscle tissue differently than by fat. As a result, the reflection of ultrasonic waves can determine certain meat characteristics, including the depth of various fat layers by determining fat boundaries or fat/tissue boundaries.

The meat producing industry has tried to use ultrasound devices for years to efficiently measure internal tissue characteristics. See, for instance, Carlson's patents which describe an ultrasonic digital backfat meter that was designed primarily for use with swine. Known devices have proven inefficient for monitoring large numbers of cattle. Measuring each animal takes too much time, and often the results are inaccurate. The speed of the measurement depends on several factors. For instance, cattle have relatively thick hair compared to other food producing animals, such as swine, which decreases ultrasonic conductivity. In order to obtain an acceptable signal, operators often clip the cattle's hair close to the skin before the ultrasound device is placed in contact therewith. This takes time and is impractical for feedlots in which many hundreds or thousands of animals must be measured, sometimes more than once, during their residency in the feedlot. When a proper conductive contact between the device and the animal is not achieved, a poor image of internal fat and muscle tissues is obtained. It is not possible to accurately measure tissue dimension or texture characteristics under such conditions.

Operators have tried spraying a conductive liquid onto the animal using a squirt bottle immediately prior to placing ultrasonic devices in contact with the so as to eliminate the need for hair clipping. This also has proven ineffective for large feed lots. Manipulating both the ultrasound device and the squirt bottle is inconvenient, and the time required to apply the liquid adds significantly to the processing time.

Another drawback associated with known devices is that the controls are not integrated at the fingertips of a single operator. More than one operator may be required to operate the device. Alternatively, a single operator may have to reset and reposition the ultrasound device after each animal is tested by moving to a location remote from the testing site where the control computer is located. As a result, known ultrasonic techniques take as long as 120 seconds to measure each animal. While this may not seem like a significant amount of time, it is considerably too long when thousands of animals must be processed daily.

SUMMARY OF THE INVENTION

A primary objective of this invention is to overcome the deficiencies of the prior art ultrasound measurement apparatuses and methods for use in measuring tissue characteristics in animals, and to provide an automated apparatus and method that performs tissue measurements quickly, easily and accurately compared to prior such apparatuses and methods.

Another specific objective of this invention is to integrate ultrasound transmission, conductive liquid dispensation and ultrasound reading functions so that the control of all functions can be placed at the fingertips of a single operator.

Another object of this invention is to provide an applicator device that includes both an ultrasound transducer and a conductive liquid dispenser.

Another object of the present invention is to provide an automated positioner for positioning ultrasound transducers, as well as other equipment, on feed animals.

Another object of the present invention is to combine automated conveyors for delivering feed animals to a tissue test zone with an automated ultrasound transducer to provide an automated system useful for evaluating the health and tissue characteristics of feed animals.

Another object of the present invention is to combine automated conveyors for delivering feed animals to a tissue test zone with an automated positioner for positioning ultrasound transducers and other equipment on feed animals to provide an automated system useful for evaluating the health and tissue characteristics of feed animals.

In general, the invention seeks to fulfill these and other objectives by providing automated tissue analysis systems comprising a conveyor for delivering a feed animal to a tissue analysis zone, an ultrasound transducer designed to conduct tissue analysis on feed animals, and a remotely actuated positioner for placing the transducer on the feed animal. The ultrasound transducer is coupled to the positioner. One embodiment of the positioner comprises a saddle, a longitudinal slide frame, a dorsal/ventral slide frame and a pivot frame for accurately positioning the transducer on the animal for conducting tissue analysis. A transducer housing is provided that includes a built-in fluid passage and dispenser for dispensing conductive fluid onto the animal from a remote fluid reservoir. A fluid pump is fluidly coupled to both the reservoir and the dispenser in the transducer housing using flexible tubing, such as TIGON tubing, so that fluid can be pumped from the reservoir to the dispenser.

Tissue analysis systems also generally include a computer or computers operably coupled to individual components of the analysis system. This allows an operator to either control the components by inputting commands to the computer, or place the computer in control of the components. The computer also can store and analyze data generated by the transducer, and any other instruments that might be used in the analysis of feed animals that can be coupled to the positioner for remote actuation. One example of such an instrument is a thermometer.

A video camera and a video/computer monitor also can be electrically coupled to the computer and the transducer. The monitor is located so that the operator can view the position of the feed animal as the animal is delivered to the tissue analysis zone by the conveyor. The operator also can view the tissue image generated by the ultrasound transducer during tissue analysis. This allows the operator to obtain a clear ultrasound image before commanding the computer, via a hand-held switch unit or joy-stick controls, to record data, such as backfat, marbling, and other measurements that can be made from the ultrasound image. One embodiment of the system includes joy-stick controls that are electrically coupled to the conveyor, saddle, transducer positioning equipment, transducer, oil dispenser pump, and the computer or computers. By actuating the joy-stick controls an operator can control all the components of the tissue analysis system.

The apparatus can be used in combination with an overall animal management system such as might be found in a feedlot. The animal management system can sort animals, promote feed efficiency and optimize shipping dates for animals, either individually or in groups.

The present invention also provides an improved method for measuring internal tissue characteristics in livestock at established and accepted locations on the animal. For example, with cattle the method comprises first providing an internal tissue characteristic evaluation apparatus substantially as described above. The ultrasound transducer is accurately positioned on the animal using a remotely actuatable positioner. The transducer preferably is positioned so that it is substantially focused on an area over the rib-eye muscle between rib 12 and 13. This is a location widely accepted for making measurements for grading and evaluating the animal with respect to internal tissue characteristics.

Conductive fluid is dispensed from the reservoir through the dispenser and onto the hide by actuating the pump. Virtually any conductive fluid will work, as long as it increases ultrasonic conductivity and is not toxic to the livestock. Soley by way of example, conductive fluids useful for the invention may be selected from the group consisting of water, vegetable oil and mineral oil. A sufficient amount of the conductive fluid, such as less than about 50 milliliters, and more typically about 30 milliliters, is dispensed onto the animal's hide to increase the ultrasonic conductivity.

An operator monitors the computer monitor until a clear image is seen. The ultrasound image is then analyzed by the computer using commercially available software. The computer also records data concerning internal tissue characteristics.

DETAILED DESCRIPTION OF THE PREFERRED EMBODIMENTS

The present tissue analysis system is especially suitable for use at feedlots for measuring particular tissue characteristics of large numbers of livestock using tissue analysis devices, such as ultrasound devices. It will be apparent that the apparatus can be used in combination with other livestock measuring systems for measuring other animal characteristics. The tissue analysis system has been designed so that positioning the feed animal, dispensing conductive fluid onto the animal, taking accurate tissue measurements, recording the data and resetting the computer can be done manually and take less than about 30 seconds, and more typically about 15 seconds, for each animal. Alternatively, the tissue analysis system can be largely automated so an operator can control the functions of the apparatus remotely or place virtually the entire system under the control of computer. Although the present invention can be used to measure meat characteristics of many species, it is particularly useful for measuring backfat, intramuscular fat and muscle of cattle.

The following paragraphs first describe an ultrasound transducer, housing for the transducer and oil dispensing system designed primarily so that an operator may manually position the transducer on a feed animal. Thereafter, an automated system for delivering an animal to the tissue analysis zone, and for automated positioning of tissue analysis device or devices on the animal, is described.

I. ULTRASOUND APPARATUS

Figure 1:
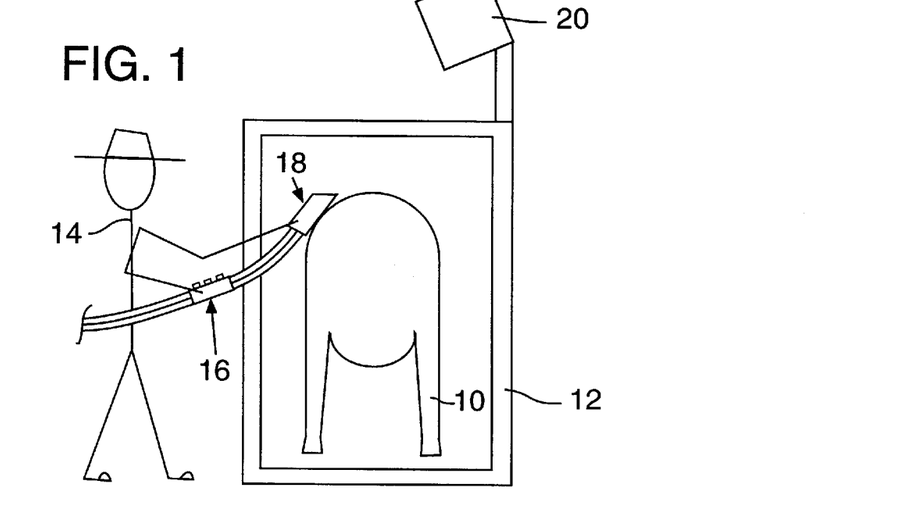
FIG. 1 is a schematic view illustrating the use of an embodiment of the ultrasound apparatus and method of the present invention in a typical animal measuring situation.

FIG. 1 shows a feed animal 10 positioned in a feedlot stall 12. Adjacent the stall is an operator 14. Operator 14 holds and operates both the switch unit 16, as well as the handpiece 18, of the present apparatus. Operator 14 also can view ultrasound images on monitor 20 during the measurement process.

A. Electric and Fluid Line Connections

Figure 2:
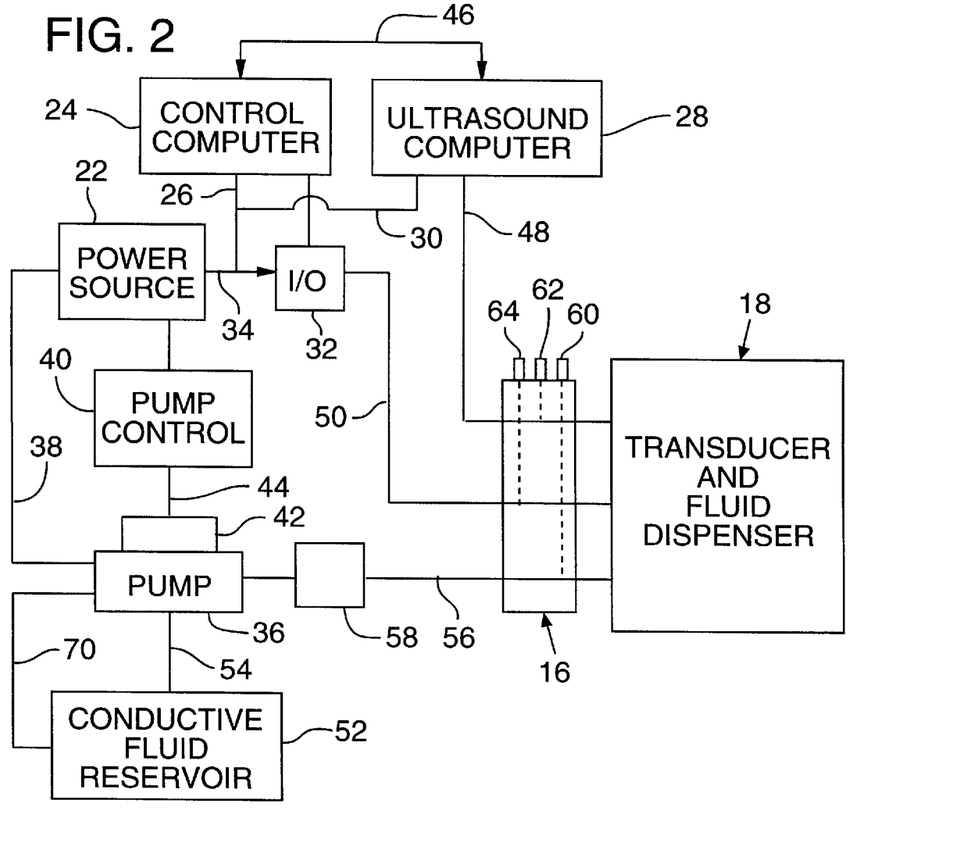
FIG. 2 is a schematic diagram showing a complete system of one embodiment of an apparatus according to the present invention.

FIG. 2 is a block diagram which illustrates certain components for an embodiment of the present invention. FIG. 2 also illustrates certain fluid and electric interconnections between these components. Power source 22 is electrically coupled to each unit requiring power. More specifically, power source 22 is electrically coupled to control computer 24 by cable 26, to ultrasound computer 28 by cable 30, to input/output module 32 by cable 34, and to pump 36 using cable 38. Pump 36 is controlled by pump control 40, which is electrically coupled to a three-way solenoid valve 42 by cable 44. A data cable 46 interconnects control computer 24 and ultrasound computer 28. FIG. 2 also illustrates that the ultrasound computer 28 is electrically coupled to switch unit 16 by cable 48. Input/output module 32 also is electrically coupled to the handpiece 18 by cable 50.

Pump 36 is fluidly coupled to reservoir 52, which contains a conductive fluid, by fluid conduit 54. Pump 36 is further fluidly coupled to switch unit 16 by fluid line 56. As shown in FIG. 2, a quick disconnect 58 may be placed in fluid line 56. This quick disconnect 58 is provided solely for convenience, and allows the pump fluid line 56 to be quickly disconnected from handpiece 18.

Each of the individual lines, namely electric cables 48, 50, and fluid line 56, are interfaced with the handpiece 18 by switch unit 16. Each of the components of the apparatus can be individually actuated using the switches 60, 62 and 64 on switch unit 16. Thus, by depressing the appropriate switch, each function of the apparatus can be actuated.

B. Components of the Test System

The components of the apparatus mentioned above will now be described in more detail. Power source 22 is a conventional piece of equipment that can be obtained commercially. Virtually any power source now known or hereafter developed that can safely power sensitive electronic apparatuses can be used to practice the invention.

Control computer 24 also is a conventional piece of equipment, and any computer which has sufficient capability to control and interface with ultrasound computer 28 will suffice. One example, without limitation, of a control computer 24 suitable for this is an IBM PC. Control computer 24 controls certain functions of the ultrasound computer 28. Commercial software is available for operating the control computer 24 to control ultrasound computer 28. One example of software suitable for this operation is sold by Animal Ultrasound Services, Inc., of Ithaca, N.Y.

The present apparatus operates by generating and transmitting into livestock an ultrasound energy pulse. This energy pulse is produced and controlled by ultrasound computer 28 and ultrasound transducer 66. Each of these components can be purchased. One example of an ultrasound apparatus that can be used to practice the invention is an ALOKA 500 V Ultrasound Computer. The ALOKA 500 V is purchased in combination with an ultrasound transducer 66 and transducer cable 68 for coupling the transducer 66 to the computer 28.

Input/output module 32 controls the signals input to and from computer 24 and to the components housed in handpiece 18. Again, the I/O module 32 is a conventional piece of equipment, and virtually any input/output module 32 will suffice for this invention. One prototype of the invention was assembled using an OPTO 22 I/O board. The OPTO 22 I/O board includes: a 1AC5Q input module; a PB16HQ circuit board; a B1 brainboard; a PBSA PP/S power supply; and an OAC5Q output module.

A pump 36 pumps conductive liquid to handpiece 18. The conductive liquid is contained in reservoir 52. Any conductive liquid likely will work for the present invention. The selection of a suitable conductive liquid will best be decided by considering, inter alia, the conductivity of the liquid, the expense of the liquid, the availability of the liquid and the toxicity of the liquid. Solely by way of example, suitable conductive liquids may be selected from the group of conductive liquids consisting of water, vegetable oil and mineral oil. Pump 36 is liquidly to conductive liquid reservoir 52 using liquid connected conduit 54, which was made from flexible TIGON tubing. A pressure equalization tube 70, also made from TIGON tubing, couples the liquid reservoir 52 and the pump 36. Pressure equalization tube 70 equalizes the pressure between the pump 36 and the reservoir 52 when the pump 36 is not in operation. This helps prevent liquid leaks from reservoir 52.

Conductive liquid is dispensed from reservoir 52 upon actuation of the pump 36. Liquid dispensation is controlled by a three-way solenoid valve 42, which is electrically coupled to pump control 40. Three-way valve 42 can be electrically actuated by switch 60, which is housed in switch unit 16. This dispenses conductive liquid from reservoir 52 through liquid conduits 54 and 56 to handpiece 18. When the pump 36 is not in use, the solenoid valve is open to pressure equalization tube 70 to equalize the pressure between the pump 36 and reservoir 52. Liquid back flow from handpiece 18 can be checked by a check valve 72, which is mechanically coupled to the handpiece 18.

Figure 3:
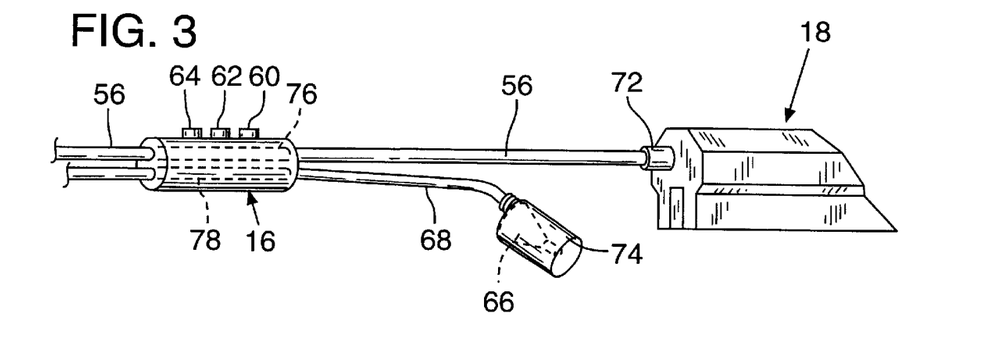
FIG. 3 is a side, partially disassembled view, illustrating the ultrasound transducer and dispensing handpiece unit of the invention.

FIG. 3 is a schematic diagram of the switch unit 16, handpiece 18, cables 48, 50, and liquid conduit 56. FIG. 3 shows transducer 66 separated from handpiece 18. FIG. 3 further shows that ultrasound transducer 66 is surrounded by a clear protective housing 74. Housing 74 performs at least two functions. First, housing 74 protects ultrasound transducer 66 from contact damage. Furthermore, protective housing 74 facilitates the positioning of transducer 66 in handpiece 18 as described below. The protective housing 74 in a prototype illustrated in FIG. 3 was made from TIGON tubing sized to tightly receive transducer 66 therein.

Figure 4:
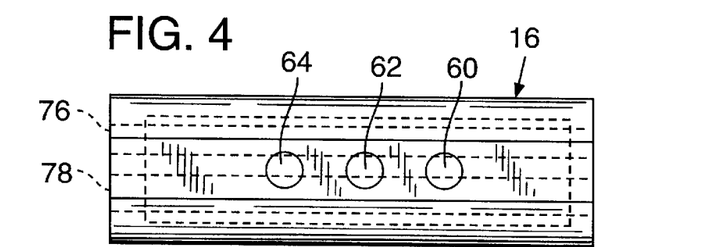
FIG. 4 is a plan view of the switch unit illustrated in FIG. 3.
Figure 5:
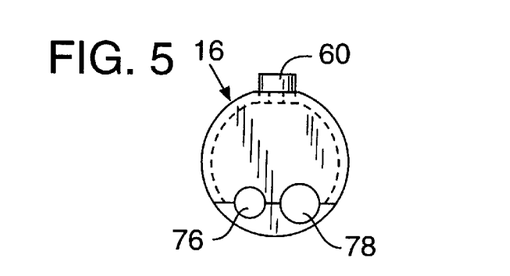
FIG. 5 is a front end view of the switch unit of FIG. 4.
Figure 9:
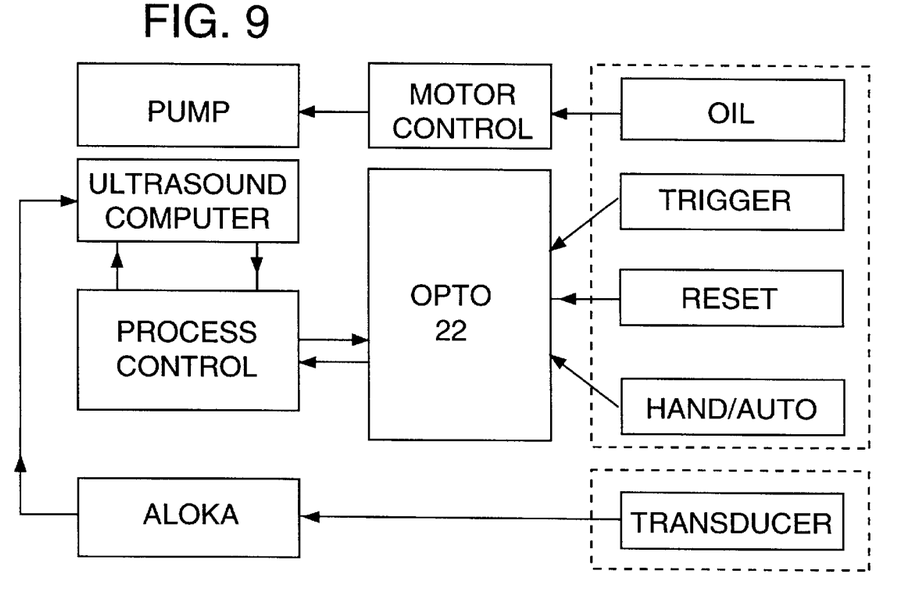
FIG. 9 is a schematic illustrating the switch unit of FIG. 4.

FIG. 4 is a schematic top plan view and FIG. 5 is an end view illustrating switch unit 16. In a prototype, switch unit 16 was made from a polypropylene block that was machined to include passages 76 and 78 therethrough. Conduit 76 provides a passage through switch unit 16 for liquid line 56. Passage 78 provides a passage through switch unit 16 for electric cables 48 and 50. Switch unit 16 includes three switches 60, 62 and 64. The switches include conductive liquid switch 60, trigger switch 62 for commanding the computer to read and analyze the image, and reset switch 64 for clearing a previous reading to prepare for rereading an animal or reading a new animal. These switches and their functions also are illustrated in FIG. 9. Switch 60 actuates liquid pump 36 so that conductive liquid from reservoir 52 is pumped through liquid line 56 and into handpiece 18. The amount of time that pump 36 operates is governed by a timer switch on pump 36 (not shown). Thus, by actuating switch 60, pump 36 is induced to pump conductive liquid from reservoir 52 for the period of time allowed by the timer switch on the pump. In a current prototype, the pump 36 is actuated for a period of less than about 5 seconds, and typically about 3 seconds, during which time less than about 50 milliliters, and more typically about 30 milliliters, is pumped from reservoir 52 to the handpiece 18.

A second switch 62 is electrically coupled to the ultrasound computer 28 by cable 48. Switch 62 activates the computer 28 to read and analyze the ultrasound image that is produced by transducer 66 as displayed on monitor 20. Thus, once the transducer 66 is correctly positioned, operator 14 depresses switch 62 to cause the computer 28 to read the ultrasound image.

A third switch 64 also is provided on switch unit 16. Switch 64 is a reset switch electrically coupled to input/output module 32 by cable 50. Switch 64 is depressed by operator 14 when the image has been read by computer 28 or when the operator wants to discard a previous reading and record a new reading of a given animal's image. This can include reapplying conductive liquid from the handpiece 18 onto the animal. resets the computer 24 and input/output module 32 this for receiving new information from a different animal 10.

Figure 6:
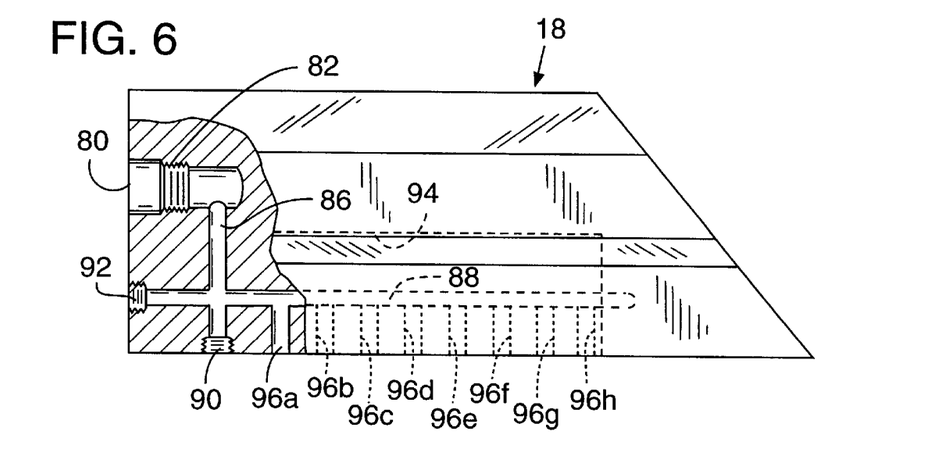
FIG. 6 is an enlarged side view of the handpieces illustrated in FIG. 3.
Figure 7:
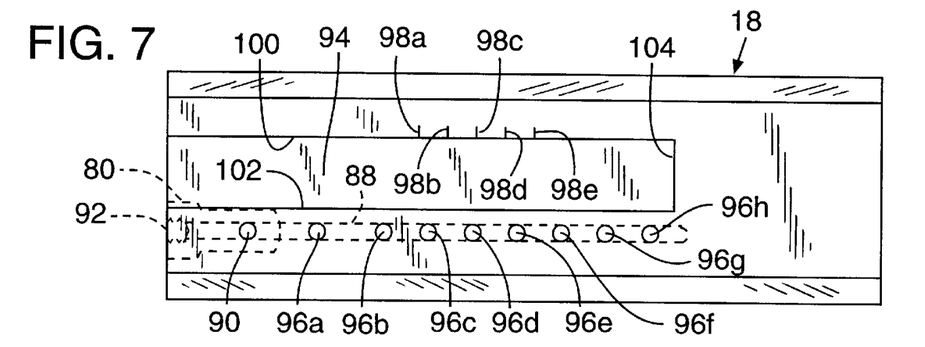
FIG. 7 is a bottom plan view of the handpiece of FIG. 3.
Figure 8:
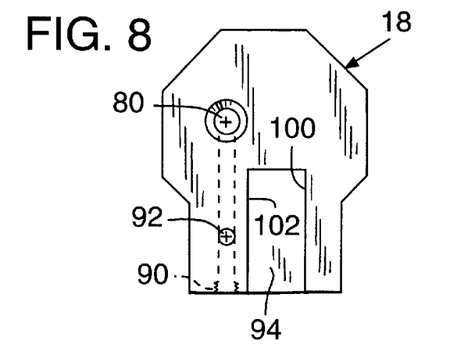
FIG. 8 is a rear end view of the handpiece illustrated in FIG. 3.

FIGS. 6–8 further illustrate the construction of handpiece 18. FIG. 6 is a side schematic view of the housing 18. Housing 18 is manufactured for this particular application, and can be manufactured from a number of suitable materials. The embodiment of a prototype illustrated in FIGS. 6–8 was manufactured from polypropylene. A block of polypropylene having suitable dimensions was obtained and then machined to have substantially the appearance illustrated in FIGS. 6–8.

More particularly, handpiece 18 is machined to include a threaded inlet 80 for receiving liquid line 56. Any suitable means for coupling the liquid line 56 to housing 18 will suffice. FIGS. 6–8 illustrate a male threaded connection 82 which is inserted into threaded portion 84 of passage 80 to couple liquid line 56 to housing 18. Housing 18 also is machined to include a passage 86 for interconnecting liquid inlet 80 and a liquid conduit 88. Liquid conduit 86 is closed using a threaded plug 90, and liquid conduit 88 is closed by a threaded plug 92.

FIG. 7 is a bottom plan view and FIG. 8 is an end view of the handpiece 18. FIGS. 7 and 8 illustrate a longitudinal slot 94 recessed in the bottom surface of the handpiece 18. Slot 94 is sized to receive the transducer 66 and protective cover 74. If, however, the transducer 66 and cover 74 are not received sufficiently tightly in slot 94 to hold the ultrasound transducer 66 securely therein, an additional polypropylene wedge (not shown) can be used to wedge ultrasound transducer 66 and protective cover 74 inside the slot 94.

FIG. 7 also illustrates that leading to and intersecting with the conduit 88 are plural output orifices 96a–96h. These orifices 96a–96h are fed by liquid line 56. Thus, as a conductive liquid enters the handpiece 18 through liquid line 56 and inlet 80, the conductive liquid flows through the passage 86, into passage 88 and thereafter through the plural orifices 96a–96h and onto animal 10. The spacing of these plural orifices 96a–96h is not critical. The embodiment illustrated in the figures has a relative spacing of approximately one-half inch between each respective orifice 96a–96h.

FIG. 7 also illustrates that the handpiece 18 includes plural position markings 98a–98e. As stated above, transducer 66 and protective cover 74 are positioned in slot 94. The transducer 66 and cover 74 are firmly wedged into the slot 94 and between side walls 100 and 102. A mid-portion of the transducer 66 is centered on one of these respective positioning marks 98a–98e depending upon the size of the animal, before the transducer is fixed in its selected position relative to end wall 104. More specifically, the smaller the animal, the closer transducer 66 is positioned to end wall 104 of slot 94.

II. LIVESTOCK MEASUREMENTS MADE USING THE PRIMARILY MANUALLY OPERATED APPARATUS

The preceding paragraphs describe a first embodiment of an apparatus useful for analyzing tissue characteristics of feed animals. This section discusses how to operate the apparatus, with particular reference to analyzing tissue characteristics in cattle.

Cattle are positioned seriatim in stall 12 during the procedure. With transducer 66 transmitting continuous ultrasound signals, operator 14 positions handpiece 18 on the back of the animal 10. The operation of the apparatus is not critically affected by the positioning of the apparatus on the back of the animal, but its positioning is important for obtaining accurate measurement data of a desired internal tissue characteristic. The transducer 66 preferably is positioned between the twelfth and thirteenth rib, and typically is focused on the rib-eye muscle approximately three-quarters of the way down the muscle. Once housing 18 is correctly positioned by an operator, switch 60 is then actuated to dispense a predetermined amount of conductive liquid from reservoir 52 onto the back of the animal 10. A sufficient amount of the conductive liquid is dispensed onto the animal 10 through line 56, passages 86 and 88, and orifices 96a–96h to obtain a clear image omn the monitor 20. If the monitor 20 shows that the transducer 66 is not correctly positioned, the transducer 66 can be removed from slot 94 in the handpiece 18 and repositioned. Once this is done for the first animal in a group of animals of the same type or general size, the transducer 66 will be adjusted for all animals in the group. The amount of liquid dispensed is not critical, except that there must be enough to obtain a clear signal from the ultrasound transducer 66. However, solely by way of example, less than about 50 milliliters, and more typically about 30 milliliters, of conductive liquid should suffice. Pump 36 can be actuated for particular predetermined lengths of time. The pump speed also can be controlled. The combination of controlling the pump speed and liquid dispensation time allows operator 14 to vary the amount of liquid dispensed upon animal 10 with each actuation of switch 60.

Once a suitable amount of conductive liquid is dispensed, which generally takes less than about 5 seconds, and more typically about 3 seconds, operator 14 then positions transducer 66 against the animal 10 over the oil and between the twelfth and thirteenth rib of the animal 10. The transducer 66 is held steady in this position while operator 14 views image monitor 20. Once a suitable image is obtained, operator 14 actuates trigger switch 62, which is electrically coupled to the ultrasound computer 28. By actuating switch 62, ultrasound computer 28 records the image and data, and calculates and records particular measurements of the animal 10. The data acquisition performed by ultrasound computer 28 is controlled by computer 24. Software is commercially available for running computer 24. This software can determine certain meat characteristics using the ultrasound data, including backfat, intramuscular marbling, and the area of a fat deposit. Thus, software can be selected to perform particular measurements on each animal, and measurement data obtained can be displayed on the monitor 20. If insufficient or inaccurate data is received from a reading, the animal can be remeasured. This is done by pressing reset switch 64 and again pressing trigger switch 62 to take a new reading.

The information obtained for each animal 10 is downloaded into computer 24. The animal 10 is then released from stall 12, and replaced by another. Prior to applying the transducer 66 to the back of the next animal, the operator actuates reset switch 64. This clears the computer 24 and prepares it to receive new data. The process is then repeated.

The primarily manual method of the present invention takes less than about thirty seconds per animal to perform, and more typically takes only about fifteen seconds. This is a significant improvement over prior ultrasound apparatuses available for use in taking animal measurements, which typically require from about forty-five seconds to two minutes. This is an unacceptably long period of time when many animals may need to be measured daily

III. AUTOMATED TISSUE ANALYSIS

The preceding paragraphs focused primarily on an ultrasound device that is manually placed on animals seriatim while conducting tissue analysis. The following paragraphs describe a more automated embodiment of a tissue analysis system.

A. General Description

Figure 10:
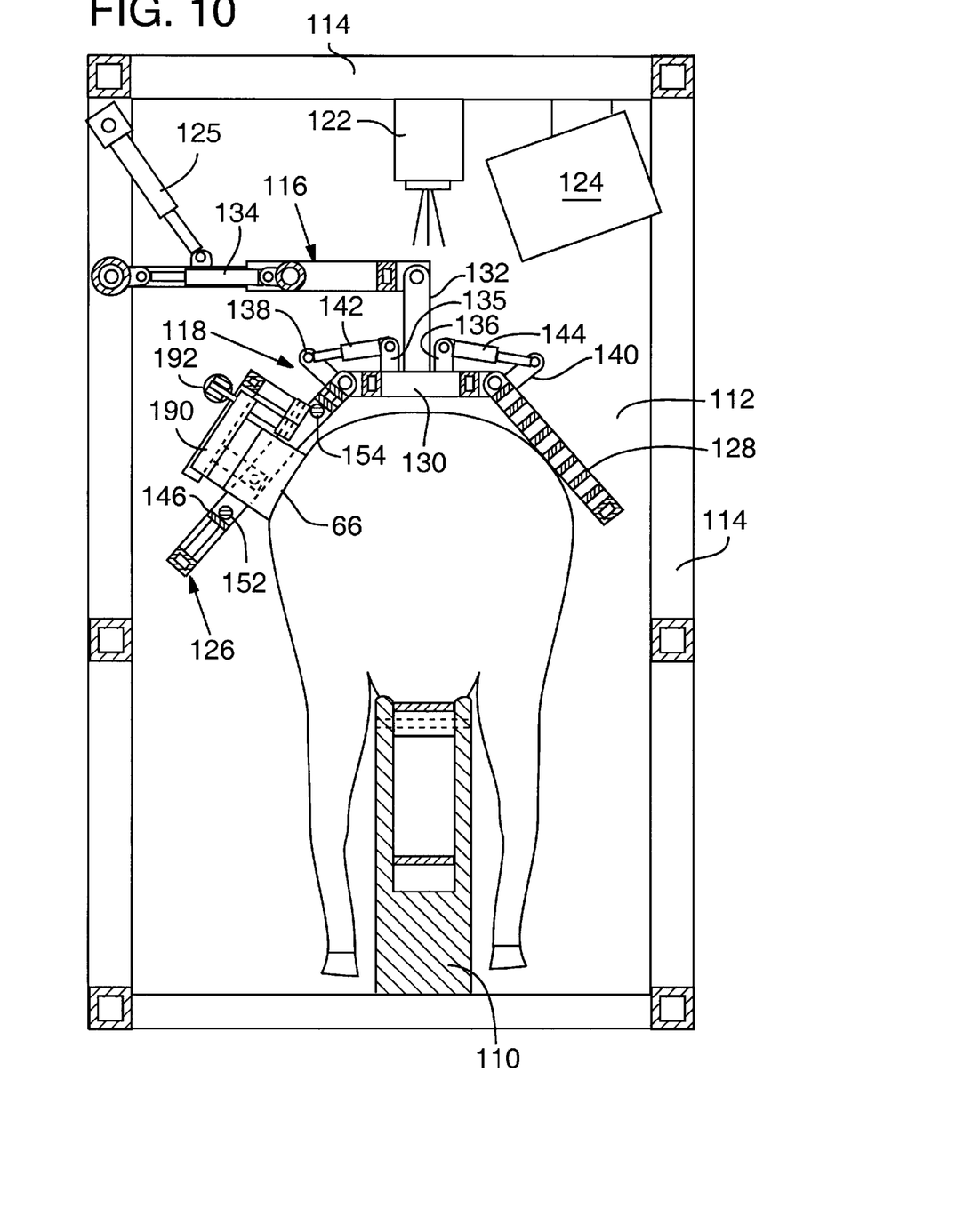
FIG. 10 is an end view of one embodiment of an automated tissue analysis system illustrating a saddle, saddle carrier arm, video camera and monitor that are used to properly position a tissue analysis device, or other devices, on an animal for analysis.

FIG. 10 illustrates one embodiment of the automated analysis system. The system includes a conveyor 110, which conveys an animal to a test zone 112 encompassed by a frame 114. Components of the analysis system are attached to frame 114, which supports the equipment adjacent the animal once it enters zone 112.

One end of a carrier arm 116 is coupled to the frame 114 and the other end to a saddle 118. Arm 116 can be actuated to carry the saddle 118 to and away from the animal once it enters zone 112. Coupled to the saddle 118 is an assembly 120 (FIG. 12) which is operably coupled to transducer 66 for positioning it correctly on the animal's back. A video camera 122 and video/computer monitor 124 are attached to the frame 114 and operably coupled to control computer 24. Video monitor 124 is located for viewing by operators while actuating the conveyor to position the animal in test zone 112, and while positioning the ultrasound transducer to obtain a good ultrasound image. Components of the tissue analysis system and their operation are described in more detail below.

B. Conveyor

Feed animals are conveyed to the tissue analysis zone 112 by a conveyor 110. The operator can watch the animal's approach on the video monitor 122 and actuate conveyor 110 to correctly position the animal in zone 112. Alternatively, computer 24 can be placed in control of the conveyor 110 to deliver animals to zone 112. Conveyor 110 not only delivers the animal from a remote location, but also renders the animal incapable of using its legs to resist. Embodiments of conveyors capable of performing both of these functions are described in Gearn et al.'s U.S. Pat. No. 5,070,818, entitled "Cattle Conveyor," ("Gearn") which is incorporated herein by reference. Gearn discloses a conveyor which supports the animal above the ground at its brisket. This renders the animal incapable of independent movement, and positions all animals to be imaged in the same relative position in zone 112, both especially important for automated imaging of live animals and obtaining meaningful comparison data. Head gates (not illustrated in FIG. 10) also can be used to further control the animal.

C. Carrier Arm and Saddle

Figure 11:
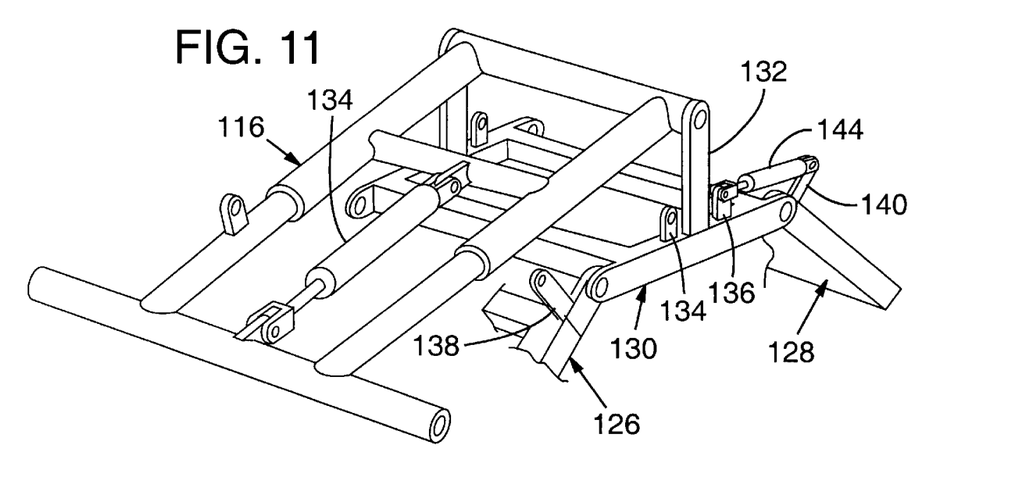
FIG. 11 is a perspective view illustrating one embodiment of a saddle having a saddle extension arm attached thereto.

One embodiment of a carrier arm 116 and saddle 118 for carrying transducer 66 to an animal located in test zone 112 is illustrated in FIGS. 10 and 11. Carrier arm 116 is pivotably coupled to the frame 114. Also coupled to the frame 114 and to the carrier arm 116 is a linear actuator 125, such as a hydraulic or pneumatic piston and cylinder. Actuator 125 can be remotely actuated for extending saddle 118 to or away from the animal.

Saddle 118 has three segments: two side frames 126, 128; and center frame 130. Side frames 126 and 128 are pivotably coupled to center frame 130. Center frame 130 contacts the dorsal region of the feed animal when the saddle 118 is properly positioned. Center frame 130 includes a bracket 132 that is attached to carrier arm 116. Carrier arm 116 includes linear actuator 134 which can be remotely actuated for extending or retracting saddle 118. Saddle 118 can be placed on the back of the animal by actuating both linear actuators 125 and 134.

Once the saddle 118 is positioned close to the animal by carrier arm 116, side frame assemblies 126 and 128 are pivoted to closely contact the animal's flanks. Attached to the top surface of center saddle frame 130 are two brackets 135 and 136. Each of the side frames 126 and 128 includes a bracket 138, 140, respectively. Brackets 135, 136, 138 and 140 are attached to two linear actuators 142, 144. By actuating the linear actuators 142, 144, the two side frames 126 and 128 are pivoted to close in or draw away from the animal's flanks.

D. Transducer Positioner

Once the saddle 118 is correctly positioned and the side frames 126 and 128 are closely contacting the sides of the animal, the transducer 66 must then be properly positioned, such as between the 12th and 13th ribs of cattle, to perform the tissue analysis. This is accomplished using remotely actuated slidable frames and a pivot frame to which the transducer is operably coupled.

As used herein, the term "positioner" refers generally to arm 116, operably coupled linear actuators 125 and 134, as well as to assemblies used to position the transducer relative to the animal. One such assembly, referred to herein as a "transducer positioner," is illustrated as assembly 120 in FIGS. 12 and 13. Transducer positioner 120 is attached to side frame 126. Transducer positioner 120 includes a longitudinal slide frame 146. "Longitudinal," when used in reference to positioning the transducer 66, refers to anterior and posterior movement generally parallel to the spine of the animal, i.e., towards the head (cephalad) or the tail (caudad). Longitudinal slide frame 146 has two cylindrical brackets 148, 150 attached. thereto for receiving slide rods 152, 154, each of which is attached to dorsal/ventral slide frame 162. Linear actuator 156 is attached to longitudinal slide frame 146 by bracket 160 and to slide frame 162 by bracket 158. Actuator 156 can be remotely actuated for sliding the longitudinal slide frame 146 on brackets 148, 150 along the slide rods 152, 154, fore and aft of the animal.

Figure 12:
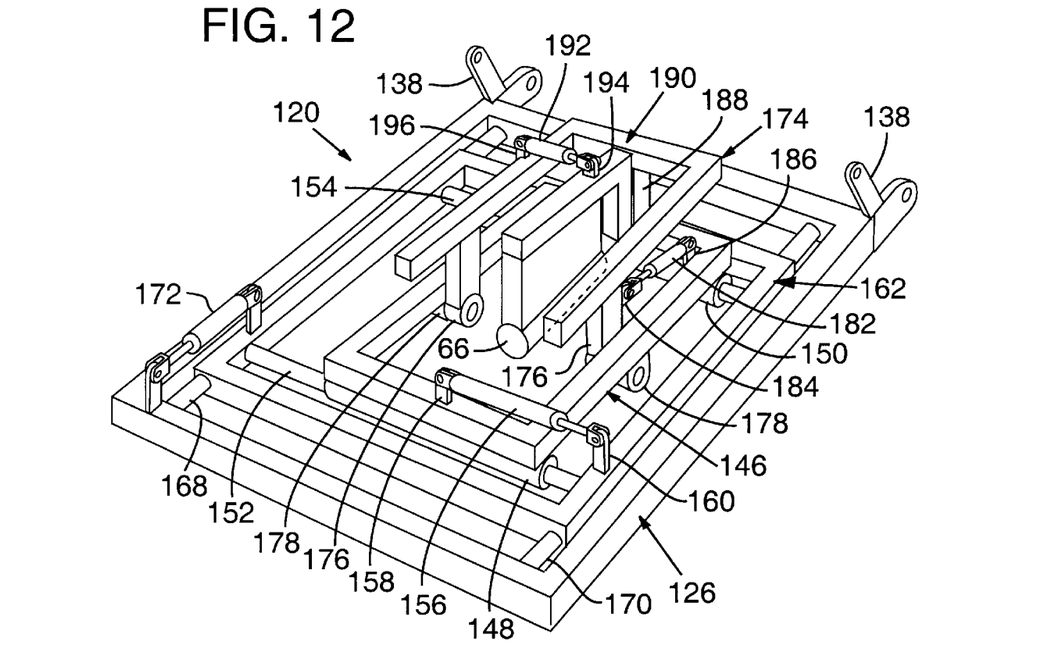
FIG. 12 is a perspective view of portion of a saddle which houses slide and pivot frames that can be operably coupled to the transducer.
Figure 13:
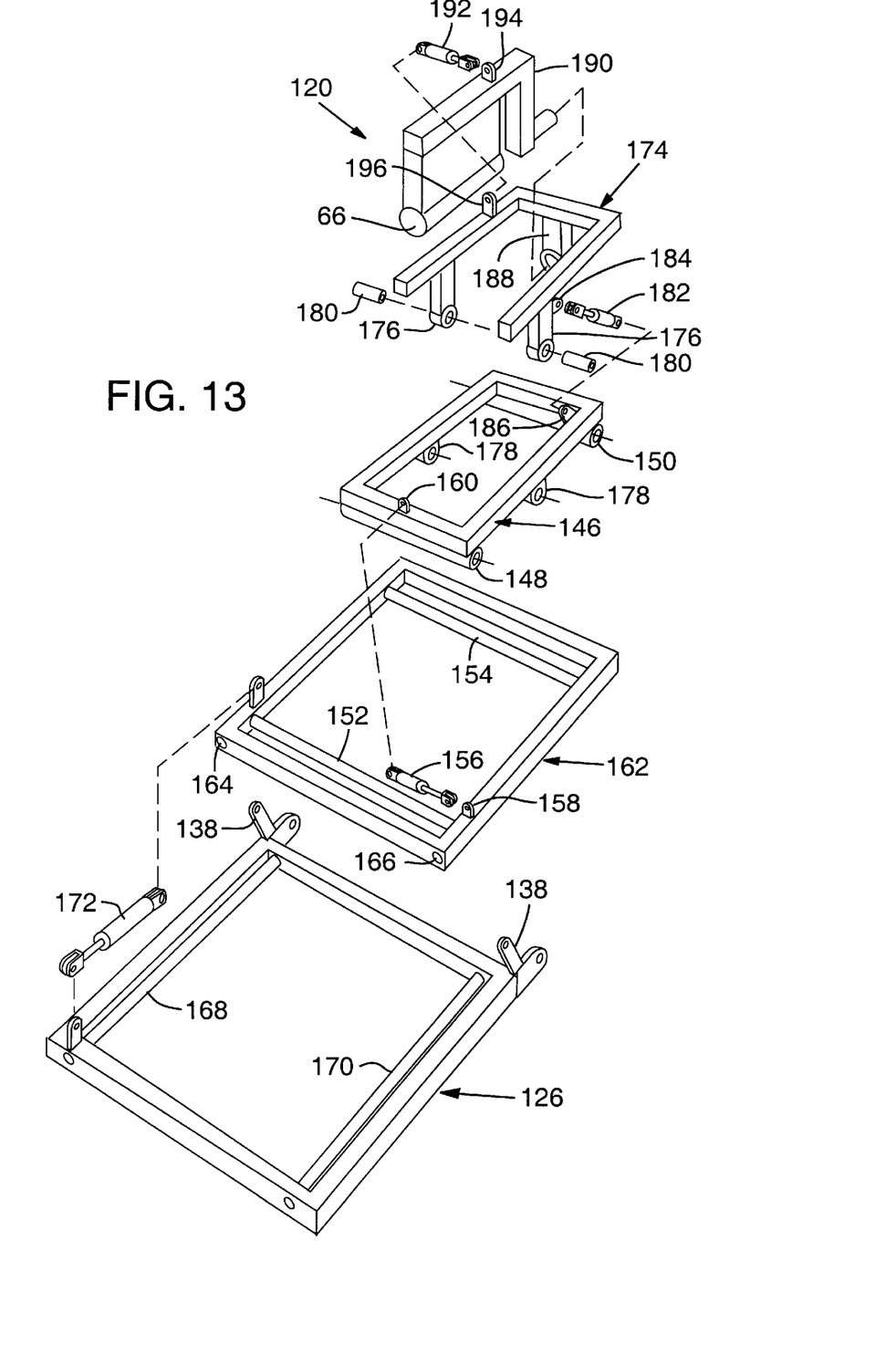
FIG. 13 is an exploded view of the apparatus illustrated in FIG. 12.

FIGS. 12 and 13 also show that the longitudinal slide frame 146 is mounted on dorsal/ventral slide frame 162, which is constructed similarly to the frame 146, and which is mounted on side frame 126. As used herein, "dorsal/ventral" refers to movement along the flanks of the animal and towards either the back (dorsal) or stomach (ventral). Slide frame 162 includes two cylindrical passages 164, 166 for receiving slide rods 168, 170, each of which is anchored to frame 126. A linear actuator 172 is attached to frame 126 and to dorsal/ventral slide frame 162. Actuator 172 can be remotely actuated for sliding the dorsal/ventral slide frame 162 along the slide rods 168, 170.

FIGS. 12 and 13 further illustrate that the slide frame 162 houses a pivot assembly 174. Attached to pivot assembly 174 are pivot assembly arms 176. Slide frame 146 further includes pivot assembly brackets 178. Pivot assembly 174 is pivotally coupled by arms 176 to assembly brackets 178 using couplers 180. Linear actuator 182 is attached to an arm 176 by bracket 184 and to the longitudinal slide frame 146 by bracket 186. Actuator 182 pivots pivot assembly 174 to control the pitch of the transducer 66, i.e., movement towards and away from the side of the animal.

Pivot assembly 174 also includes a transducer bracket 188 for coupling the transducer 66 to the pivot assembly 174. For the automated tissue analysis system transducer 66 is coupled to a transducer housing 190. Housing 190 is constructed similarly to housing 74, but is designed to be received by bracket 188. Housing 190 is pivotally coupled to transducer bracket 188 as shown in FIG. 13. Moreover, a linear actuator 192 is coupled to the transducer housing 190 by bracket 194 and to pivot assembly 174 by pivot assembly bracket 196. Actuator 192 can be remotely actuated to control the roll of assembly 174 (i.e., anterior and posterior pivoting of the transducer face) and hence the roll of transducer 66.

E. Joy-Stick Control

Figure 14:
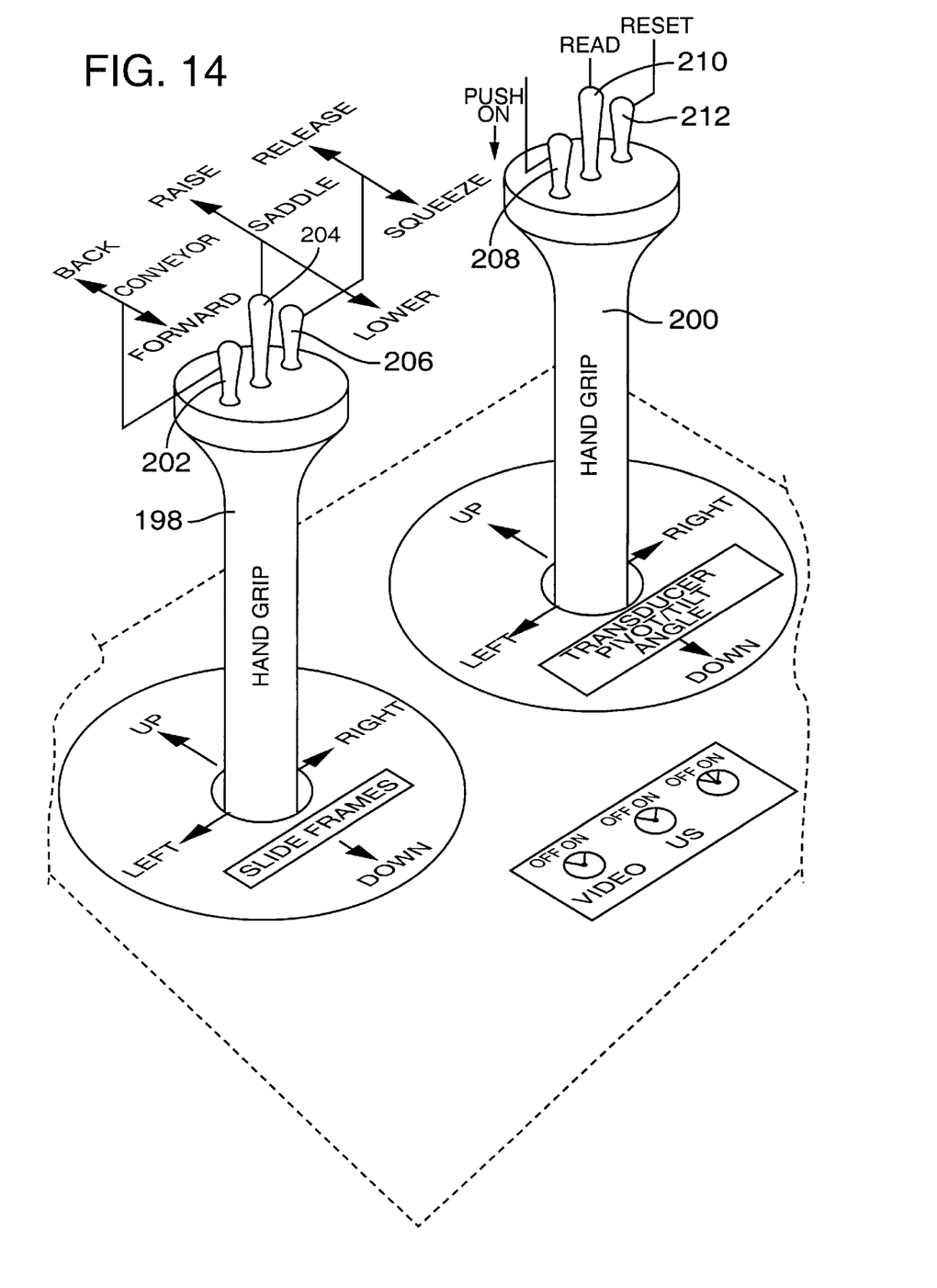
FIG. 14 illustrates joy-stick controls operably coupled to the control computer and other components of the tissue analysis system.

FIG. 14 illustrates joy-stick controls 198, 200 that are electrically coupled to the control computer 24 and to each of the components discussed above. The illustrated embodiment of joy stick 198 includes switches 202, 204 and 206. Switches 202, 204 and 206 provide for electrically actuating the conveyor 110 (switch 202), linear actuators for placing the saddle 118 on the animal, such as linear actuators 125 and 134 (switch 204), and linear actuators coupled to frames 126 and 128 for squeezing the animal, such as linear actuators 142 and 144 (switch 206). Furthermore, joy stick 198 itself can be moved to activate the longitudinal linear actuator 156 and the dorsal/ventral linear actuator 172 to position the transducer 66 correctly between the 12th and 13th rib of the animal.

Joy stick 200 includes switches 208, 210 and 212 which are electrically coupled to the pump 36 (switch 208), the transducer 66 (switch 210) and the control computer or transducer computer if a separate computer is used to control the transducer (switch 212). Joy stick 200 also can be itself moved to actuate linear actuators 182 and 192 to further adjust the pitch and roll of the transducer 66. Thus, an operator located remotely from test zone 112 can actuate each component of the tissue analysis system to: (1) deliver the animal to the test zone 112 by controlling the movement of conveyor 110; (2) actuate linear actuators coupled to carrier arm 116 to lower the saddle 118 onto the animal's back; (3) actuate linear actuators 142 and 144 to pivot the side frames 126, 128 to squeeze the animal's sides; (4) actuate longitudinal linear actuator 156 to correctly position the longitudinal slide frame 146; (5) actuate dorsal/ventral linear actuator 172 to correctly position the dorsal/ventral slide frame 162; (6) actuate the linear actuator 182 to pivot the pivot assembly 174; (6) activate pump 36 to dispense oil onto the animal; (7) activate the transducer 66 to analyze the animal's internal tissue; (8) reset the transducer 66; and (9) control the control computer or the ultrasound computer to reset the transducer 66 for further measurements and to store, record and analyze data.

F. Power Connections

Figure 15:
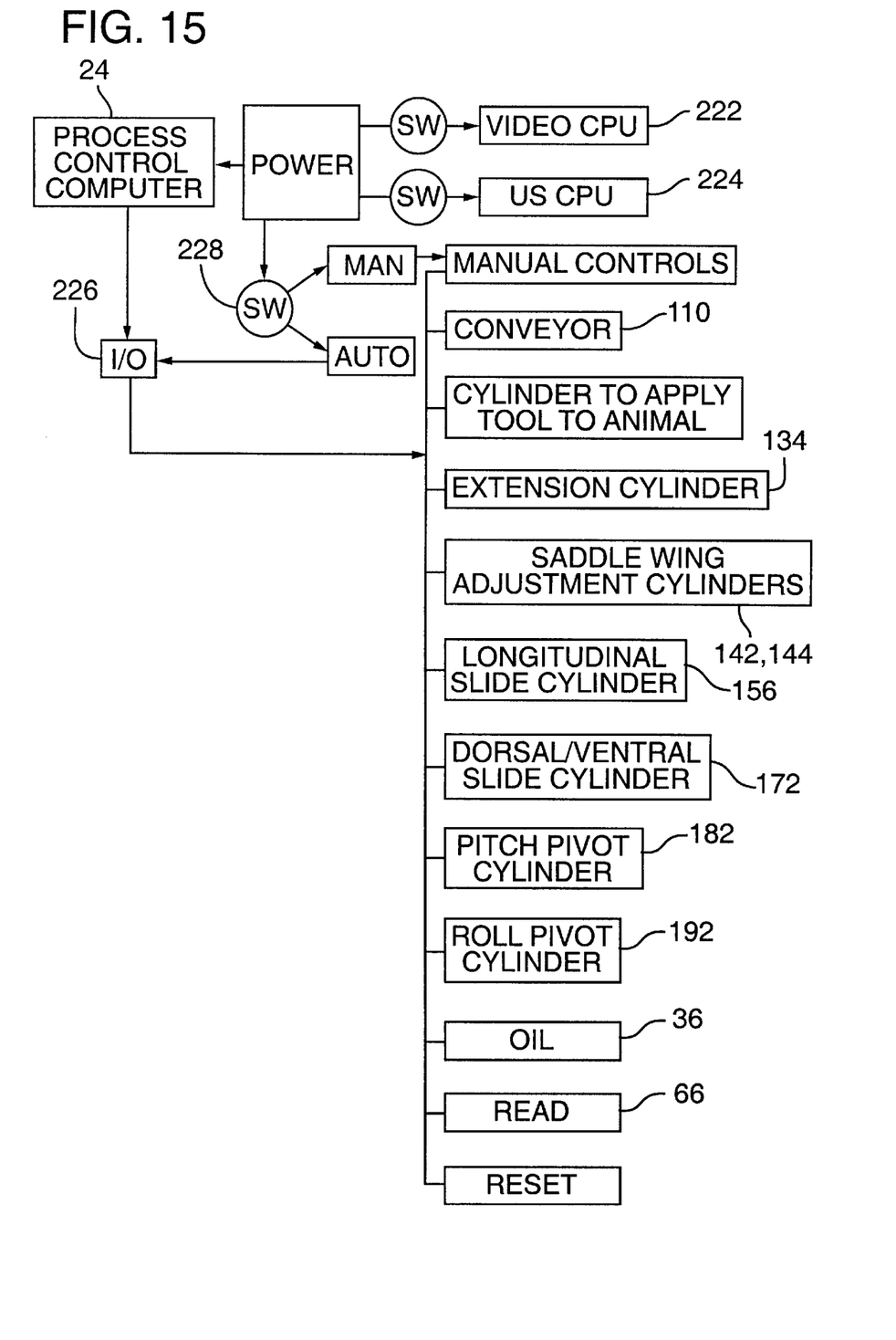
FIG. 15 is a block diagram illustrating the power connections for components of the automated tissue analysis system.

FIG. 15 illustrates the power connections used to connect each of the components described above. Electrical power is provided to a process control computer 24, a video CPU and an ultrasound transducer CPU 224. The process control computer also is electrically coupled to an input/output device (I/O) 226 for interfacing each of the components comprising the tissue analysis system to the control computer. More specifically, the I/O device allows communication between the control computer and the following: (1) conveyor 110 for delivering the animal to the tissue analysis zone 112; (2) the linear actuator 125 lowers the saddle 118 onto the animal; (3) linear actuator 134 for extending saddle 118 in a direction transverse to the longitudinal axis of the animal; (4) linear actuators 142 and 144 to adjust side saddle frames 126 and 128; (5) longitudinal linear actuator 156 and dorsal/ventral linear actuator 172 for positioning the transducer 66 to conduct tissue analysis, such as between the 12th and 13th rib of cattle; (6) linear actuators 182 and 192 to adjust the roll and yaw, respectively, of the transducer 66; (7) pump 36 so that conductive fluid may be dispensed from reservoir 52 onto the animal; and (8) transducer 66 to begin tissue analysis, and to reset the transducer for subsequent analysis. Moreover, FIG. 15 shows that a switch 228 is included in the system so that the test system can be run either manually or in an automated mode by actuating the manual/auto switch.

G. Software and Automated Operation

The operation of the present device is under the control of a process control computer and video and ultrasound CPUs. The steps executed by the software which controls these computers are shown in the block diagram of FIG. 16, which indicates that a menu system likely would be provided for the benefit of the operator. Once the program is initiated by an operator selecting the desired program from the menu system at 230, ultrasound transducer 66 and video camera 122 are turned on at 232, 234. Conveyor 110 is then started at 236 to position the animal beneath the video camera 122. Incremental adjustments to the animal's position can be made and such adjustments monitored at 238 in video monitor 124 by intermittently activating conveyor 110 via switch 240 until the animal is correctly positioned in test zone 112 for receiving the saddle 118.

Figure 16:
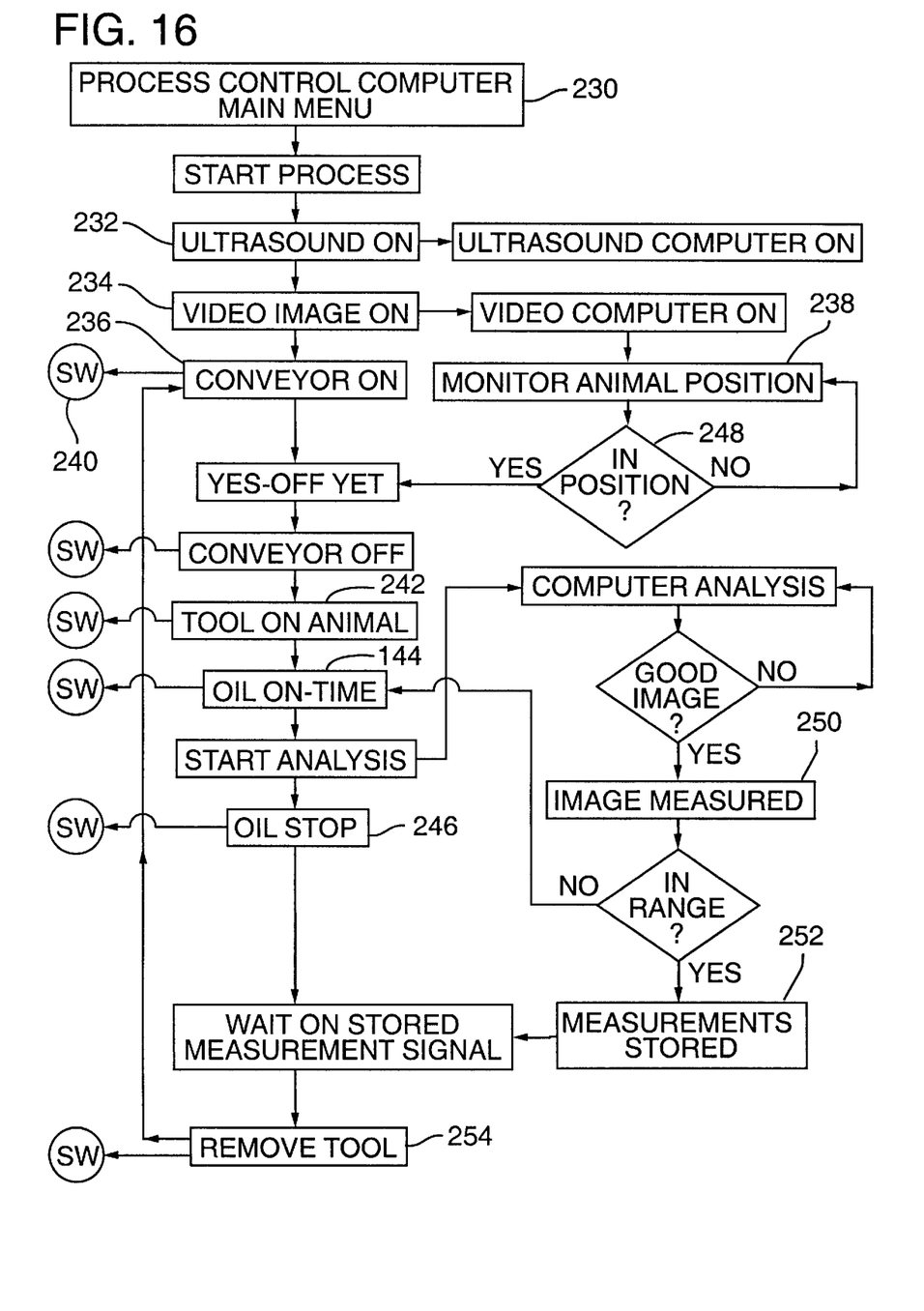
FIG. 16 is a block diagram illustrating software process steps.

Linear actuators are then activated to lower the saddle 118 onto the animal and squeeze the animal's sides at 242. Pump 36 is then activated at 244 to dispense conductive liquid on the back of the animal from reservoir 52. Once the oil is dispensed, transducer 66 is then activated at 246 and the tissue image displayed on video monitor 124. A determination is then made, either by the operator or by the control computer, whether a good ultrasound image is obtained at 248. If the transducer 66 is not producing a good image, then its position is adjusted by actuating any or all of the linear actuators 156, 172, 182 and 192. The positioning of the transducer 66 is continued until a good ultrasound image is obtained at 250.

A determination is then made, either by the operator or by the control computer, whether the tissue measurements obtained by the ultrasound transducer are within a predetermined range. If not, then more conductive oil may be applied to the animal, and the positioning steps repeated. Once the tissue measurements are within the predetermined range, such measurements are then stored at 252. The saddle 118 is then removed from the animal's back at 254, and the next animal moved into place by activating the conveyor 110.

The present invention has been described with reference to preferred embodiments. It should be understood that certain modifications may be made thereto without departing from the invention. I claim as my invention the embodiments described herein and all such modifications and equivalents as come within the true spirit and scope of the following claims.

I claim:

1. A system for measuring internal tissue characteristics in feed animals, comprising:

a tissue analysis device; and a remotely actuatable positioner coupled to the analysis device for positioning the device along a longitudinal axis of the feed animal and along flanks of the animal in a dorsal-to-ventral or in a ventral-to-dorsal manner to allowing] allow for tissue analysis.

2. The system according to claim 1 and further including a control computer electrically coupled to the analysis device and positioner for controlling the functions of the analysis device and for positioning the analysis device on the animal in a manner allowing for tissue analysis.

3. The test system according to claim 1 and further including a conveyor for delivering the animal to the tissue analysis zone from a remote location.

4. The test system according to claim 3 wherein the conveyor also prevents independent movement of the animal as the animal is delivered to the tissue analysis zone.

5. The system according to claim 1 wherein the tissue analysis device is an ultrasound transducer.

6. The system according to claim 5 wherein an ultrasound transducer housing includes a conductive fluid dispenser for dispensing liquid from a reservoir onto the animal.

7. The system according to claim 1 wherein the positioner includes a longitudinal slide frame and a linear actuator operably coupled thereto for adjusting the position of the tissue analysis device along the longitudinal axis of the animal.

8. The system according to claim 1 wherein the positioner includes a dorsal/ventral slide frame and a linear actuator operably coupled thereto for adjusting the position of the tissue analysis device along flanks of the animal in a dorsal-to-ventral manner or in a ventral-to-dorsal manner.

9. The system according to claim 1 wherein the positioner includes a pivot frame and a linear actuator coupled thereto for adjusting the pitch of the tissue analysis device.

10. The system according to claim 1 wherein the transducer is pivotally coupled to the positioner and the positioner further includes a linear actuator for adjusting the roll of the tissue analysis device.

11. The system according to claim 1 wherein the positioner further comprises:

a longitudinal slide frame and a linear actuator operably coupled thereto for adjusting the position of the tissue analysis device along the longitudinal axis of the animal;

a dorsal/ventral slide frame and a linear actuator operably coupled thereto for adjusting the position of the tissue analysis device along flanks of the animal in a dorsal-to-ventral manner or in a ventral-to-dorsal manner; and a pivot frame and a linear actuator coupled thereto for adjusting pitch of the tissue analysis device.

12. The system according to claim 11 wherein the transducer is pivotally coupled to the positioner and to a linear actuator for adjusting the roll of the tissue analysis device.

13. A system for measuring internal tissue characteristics in feed animals, comprising:

a conveyor for delivering animals to a tissue analysis zone and rendering the animals incapable of independent movement;

a carrier arm for placing a saddle on feed animals in the tissue analysis zone;

an ultrasound transducer coupled to the saddle;

an ultrasound transducer positioner operably coupled to the ultrasound transducer for positioning the transducer on an animal in a manner allowing for tissue analysis; and a control computer electrically coupled to the carrier arm, saddle, ultrasound transducer and ultrasound transducer positioner for positioning the carrier arm, saddle, and ultrasound transducer, and for controlling the functions of the transducer.

14. The system according to claim 13 wherein the ultrasound transducer positioner comprises (1) a longitudinal slide frame and a linear actuator operably coupled thereto for adjusting the position of the transducer along the longitudinal axis of the animal, (2) a dorsal/ventral slide frame and a linear actuator operably coupled thereto for adjusting the position of the transducer along flanks of the animal in a dorsal-to-ventral manner or in a ventral-to-dorsal manner, (3) a pivot frame and a linear actuator coupled thereto for adjusting pitch of the tissue analysis device, and (4) wherein the transducer is pivotally coupled to the positioner and to a linear actuator for adjusting roll of the tissue analysis device.

15. A method for measuring internal tissue characteristics in animals, comprising:

conveying animals seriatim to a tissue analysis zone;

providing an ultrasound transducer comprising a reservoir containing a conductive liquid, an ultrasonic transducer, a housing for the transducer further comprising a dispenser for dispensing conductive liquid from the reservoir onto the livestock, a liquid pump liquidly connected to both the reservoir and the dispenser;

providing a remotely actuatable positioner coupled to the transducer for positioning the transducer properly on an animal in a manner allowing for tissue analysis;

positioning the ultrasound transducer on an animal's hide so that the transducer is substantially focused on a rib-eye muscle;

dispensing conductive liquid from the reservoir through the dispenser and onto the hide by actuating the pump; and obtaining an ultrasound image.

16. The method according to claim 15 wherein the conductive liquid is selected from the group consisting of water, vegetable oil and mineral oil.

17. The method according to claim 15 wherein the animals are cows, and the transducer is positioned between rib 12 and 13.

18. The method according to claim 15 wherein the step of dispensing comprises dispensing a sufficient amount of the conductive liquid to increase the ultrasonic conductivity.

19. The method according to claim 18 wherein less than about 50 milliliters of conductive liquid are dispensed.

20. The method according to claim 15 and further including the step of viewing an ultrasound image on a monitor during any or all of the steps of positioning the transducer, dispensing the liquid and obtaining an ultrasound image.

21. A system for measuring internal tissue characteristics in feed animals, comprising:

a conveyor for delivering a feed animal to a tissue analysis zone from a remote location;

a tissue analysis device; and a remotely actuatable positioner coupled to the analysis device for positioning the device on the animal at the tissue analysis zone in a manner allowing for tissue analysis.

* * * * *